US009688595B2

(12) United States Patent
Suryanarayan et al.

(10) Patent No.: US 9,688,595 B2
(45) Date of Patent: Jun. 27, 2017

(54) PROCESS OF PRODUCTION OF RENEWABLE CHEMICALS AND BIOFUELS FROM SEAWEEDS

(71) Applicants: Shrikumar Suryanarayan, Bangalore (IN); Sri Sailaja Nori, Chennai (IN); Sawan Kumar, Chennai (IN); Nelson Vadassery, Chennai (IN); Sowmyalakshmi Balendiran, Chennai (IN); Sayash Kumar, Chennai (IN)

(72) Inventors: Shrikumar Suryanarayan, Bangalore (IN); Sri Sailaja Nori, Chennai (IN); Sawan Kumar, Chennai (IN); Nelson Vadassery, Chennai (IN); Sowmyalakshmi Balendiran, Chennai (IN); Sayash Kumar, Chennai (IN)

(73) Assignee: Sea6 Energy Private Ltd., Bangalore (IN)

( * ) Notice: Subject to any disclaimer, the term of this patent is extended or adjusted under 35 U.S.C. 154(b) by 195 days.

(21) Appl. No.: 14/349,995

(22) PCT Filed: Oct. 4, 2012

(86) PCT No.: PCT/IB2012/001967
§ 371 (c)(1),
(2) Date: Apr. 4, 2014

(87) PCT Pub. No.: WO2013/050860
PCT Pub. Date: Apr. 11, 2013

(65) Prior Publication Data
US 2014/0273098 A1    Sep. 18, 2014

(30) Foreign Application Priority Data
Oct. 5, 2011    (IN) .......................... 3458/CHE/2011

(51) Int. Cl.
| C12P 19/00 | (2006.01) |
| C07C 29/74 | (2006.01) |
| C12P 19/02 | (2006.01) |
| C10L 1/02 | (2006.01) |
| C10L 3/08 | (2006.01) |
| C13K 1/02 | (2006.01) |
| C12P 5/02 | (2006.01) |
| C12P 7/06 | (2006.01) |
| C12P 7/10 | (2006.01) |
| C12P 7/16 | (2006.01) |
| C12P 7/64 | (2006.01) |
| C13K 13/00 | (2006.01) |
| C10G 1/00 | (2006.01) |

(52) U.S. Cl.
CPC ............ *C07C 29/74* (2013.01); *C10G 1/00* (2013.01); *C10L 1/02* (2013.01); *C10L 3/08* (2013.01); *C12P 5/023* (2013.01); *C12P 7/06* (2013.01); *C12P 7/10* (2013.01); *C12P 7/16* (2013.01); *C12P 7/649* (2013.01); *C12P 7/6463* (2013.01); *C12P 19/00* (2013.01); *C12P 19/02* (2013.01); *C13K 1/02* (2013.01); *C13K 13/007* (2013.01); *C12P 2201/00* (2013.01); *C12P 2203/00* (2013.01); *Y02E 50/10* (2013.01); *Y02E 50/13* (2013.01); *Y02E 50/16* (2013.01); *Y02E 50/17* (2013.01); *Y02E 50/343* (2013.01)

(58) Field of Classification Search
CPC ... C10G 1/00; C07C 29/74; C10L 1/02; C10L 3/08; C12P 19/00; C12P 10/02; C12P 2201/00; C12P 2203/00; C12P 5/023; C12P 7/06; C12P 7/10; C12P 7/16; C12P 7/6463; C12P 7/649; C13K 13/007; C13K 1/02; Y02E 50/10; Y02E 50/13; Y02E 50/16; Y02E 50/17; Y02E 50/343
See application file for complete search history.

(56) References Cited

U.S. PATENT DOCUMENTS

| 6,893,479 B2 | 5/2005 | Eswaran et al. |
| 7,479,167 B2 | 1/2009 | Markels, Jr. |
| 7,985,267 B2 | 7/2011 | Markels, Jr. |
| 2008/0145380 A1* | 6/2008 | Teas ................. A61K 36/03 424/195.17 |
| 2015/0216894 A1* | 8/2015 | McCarthy ............ A61K 47/12 514/55 |

FOREIGN PATENT DOCUMENTS

| CN | 101787300 A | 7/2010 |
| WO | WO 2008/105618 A1 | 9/2008 |
| WO | WO 2010/098585 A2 | 9/2010 |
| WO | WO 2011/027360 A1 | 3/2011 |
| WO | WO 2013/050860 A9 | 4/2013 |

OTHER PUBLICATIONS

Soe-Htun Reports US Marine Biol. Institute, Kochi Univ. (1986) 8: 9-13; abstract.*

(Continued)

*Primary Examiner* — Susan Hanley
(74) *Attorney, Agent, or Firm* — Brinks Gilson & Lione

(57) ABSTRACT

A scalable and sustainable process for production of renewable chemicals and biofuel from seaweed in its own juices or in seawater without desalination of the seaweeds is provided herein. The process as disclosed in the preset invention is an eco-friendly process for production of renewable chemicals and biofuel with an easy method of disposing of the waste streams. Further, the process as disclosed in the present invention is cost effective, suitable since transporting and storing the raw material obtained in the form of slurry of the seaweeds because of its lesser bulk is easy, easier handling due to its free flowing nature and its direct use for further processing to obtain renewable chemicals and/or biofuel.

25 Claims, 4 Drawing Sheets

(56) References Cited

OTHER PUBLICATIONS

Floreto et al. Botanica Marina (1998) 41: 467-481.*
Definition of slurry from http://www.dictionary.com/browse/slurry?.qsre=2446, downloaded Mar. 23, 2016.*
Gotovets et al. Vestnik Dal'nevostochnogo Filiala Akademii Naul USSR (1937) No. 22, pp. 53-61, abstract only.*
Gotovets et al. bulletin of the Far Eastern Branch of the Academy of Sciences of the USSR (1937) 22: 53-61, in Russian.*
English translation of Gotovets et al. bulletin of the Far Eastern Branch of the Academy of Sciences of the USSR (1937) 22: 53-61, translated by FLS, Inc. Sep. 2016.*
Fabian et al. J. Bacteriology (1929) 18: 265-291.*
Fabian et al. Food Technol. (1953) 7: 212-217.*
Khambhaty et al., "Bioethanol from Macroalgal Biomass: Utilization of Marine Yeast for Production of the Same," *Bioenerg. Res*, 6:188-195 (2013).
Floreto and Teshima, "The Fatty Acid Composition of Seaweeds Exposed to Different Levels of Light Intensity and Salinity," *Botanica Marina*, 41:467-481 (1998).
Goh and Lee, "A visionary and conceptual macroalgae-based third-generation bioethanol (TGB) biorefinery in Sabah, Malaysia as an underlay for renewable and sustainable development," *Renewable and Sustainable Energy Reviews*, 14:842-848 (2012).

* cited by examiner (A) (B)

PROCESS OF PRODUCTION OF RENEWABLE CHEMICALS AND BIOFUELS FROM SEAWEEDS

RELATED APPLICATIONS

The present patent document is a §371 national phase application based on International Application Serial No. PCT/IB2012/001967, filed Oct. 4, 2012, designating the United States and published in English, which claims priority to Indian Application Serial No. 3458/CHE/2011, filed Oct. 5, 2011, which are hereby incorporated by reference.

FIELD OF INVENTION

The present invention relates to the field of production of renewable chemicals and biofuel from biomass in particular from seaweed biomass. More particularly the present invention relates to a process for producing renewable chemicals and/or biofuel from seaweed without desalination of the seaweed and/or using seawater as the natural processing medium instead of fresh water.

BACKGROUND OF THE INVENTION

The increasing demand of fuel leading to fuel shortages along with increased energy costs and environmental concerns have created a need for alternative energy sources, particularly those that are renewable. Biofuels have become a popular alternative fuel source because they are renewable.

As the demand for Biofuel and renewable industrial chemicals grows, so does the demand for Biomass. At very large scales of operation, the consolidation and transportation of large volumes of low density biomass overland is expensive and consumes a significant part of the energy generated. Biomass is grown on arable land, using large amounts of freshwater for irrigation and fertilizer. At a certain scale therefore, the demand for Biomass for Energy and industrial use begins to compete with Agriculture for the purpose of food production leading to unacceptable stresses in the food supply chain with a consequent escalation of food prices. In addition, the processing of Biomass to Biofuel and renewable chemicals at very large scales also involves the use of extremely large quantities of fresh water for hydrolysis the biomass as well as for fermentation. Given the increasing shortage of fresh water resources, this represents a scalability issue. Furthermore any such industrial process results in the formation of large quantities waste streams which need to be treated and disposed of in an environmentally acceptable manner. All of these issues could be prohibitive barriers in implementing such Biomass based processes widely and on a large scale.

Biomass produced from traditional agriculture or forestry operations has been the main source of fermentable sugars for the production of a variety of useful products including renewable industrial chemicals and Biofuel. The process of converting any kind of terrestrial biomass to such products generally involves collection and transportation of the biomass to a central processing location, pre-treatment of the biomass to make it amenable to further conversion, optionally followed by a treatment to break down the carbohydrate component of this biomass to fermentable sugars, followed by fermentation of these sugars with an appropriate strain of microorganism to produce the renewable industrial chemical or biofuel of interest.

Crops such as corn have been considered for producing biofuels because they are capable of being converted to alcohol. When ethanol is made from corn, it arguably takes more energy to produce the ethanol than is actually obtained from it. Also, using a grain such as corn for fuel precludes it from being used as food for humans. Corn production is also hard on the land because it erodes the soil. However, a biomass such as algae is capable of creating a fuel with a high power density, is renewable and, unlike corn, does not take away a food source from humans and livestock. The alternative to terrestrially grown Biomass is to use aquatic photosynthetic biomass such as seaweed that can be easily grown in the sea, without using freshwater and fertilizers.

The energy in biomass can be accessed by turning the raw materials, or feedstocks, into a usable form. Transportation fuels made from biomass through biochemical or thermochemical processes are known as biofuels which include ethanol, methanol, biodiesel, biocrude, and methane.

Ethanol is the most widely used biofuel today. Ethanol is an alcohol, and most is made using a process similar to brewing beer, in which starch crops are fermented into ethanol, which is then distilled into its final form. Ethanol made from cellulosic biomass materials instead of traditional feedstocks (starch crops) is called $2^{nd}$ generation bio-ethanol. Ethanol can be used in its pure form (neat), as a blend with gasoline, or as a fuel for fuel cells. Ethanol is added to gasoline as an oxygenate to improve vehicle performance and reduce air pollution.

Methanol is also an alcohol that can be used as a transportation fuel. Currently produced using natural gas, methanol can be produced from biomass through a two-step thermochemical process. First the biomass is gasified to produce hydrogen and carbon monoxide. These gases are then reacted to produce methanol. Methanol can be used in its pure form, as a feedstock for the gasoline additive methyl tertiary butyl ether (MTBE), or as fuel for fuel cells.

Biodiesel is a renewable diesel fuel substitute that can be made by chemically combining any natural oil or fat with an alcohol (usually methanol). Many vegetable oils, animal fats, and recycled cooking greases can be transformed into biodiesel and there are many different ways to do it. Biodiesel can be used neat or as a diesel additive and is typically used as a fuel additive in 20% blends (B20) with petroleum diesel in compression ignition (diesel) engines. Other blend levels can be used depending on the cost of the fuel and the desired benefits.

Biocrude is a product similar to petroleum crude and can be produced from biomass using a fast pyrolysis process. Biocrude is formed when the biomass derived oil vapors are condensed. Catalytic cracking then converts biocrude into transportation fuels.

Methane is the major component of compressed natural gas, an alternative transportation fuel. Methane, in a blend of other gases, can be produced from biomass by a biochemical process called anaerobic digestion.

U.S. Pat. No. 6,893,479 describes a process to crush or homogenize the red seaweed to produce filterable slurry which can be separated to give the salt containing fluids and granules containing carrageenan. Removal of the sap is a means of efficiently producing dry seaweed granules and sap separately.

U.S. Pat. No. 7,479,167 describes a method for production of biofuels from the open ocean, wherein the method comprises testing the currents to determine that a seaweed biomass remains in a zone suitable for harvesting, harvesting a portion of the biomass and processing a portion of the harvested biomass to produce useful components of biofuels. The patent further describes a method for the producing an increased seaweed biomass to be proceeds into a biofuel from the surface of the ocean waters using the comprising the steps of testing a water surface of an ocean to determine a time period that the water will remain for a biomass generation, and testing the currents to determine that any biomass produced remains in a zone suitable for harvesting; testing the water surface to determine a first nutrient that is missing to a first extent that limits the growth of a first plant life; applying the first missing nutrient in a form that remains available to the first plant life; harvesting a first harvested portion of an increased biomass of the first plant life that results from the applying; and removing a first returnable portion from the first harvested portion to leave a remainder of the first harvested portion, and spreading the first returnable portion on the water surface.

U.S. Pat. No. 7,985,267 describes a method of producing biofuel from the surface of the ocean waters comprising the steps testing a water surface of an ocean to determine a time period that the water will remain for a biofuel generation; testing the water surface to determine a first nutrient that is missing to a first extent that limits the growth of a first plant life; applying the first missing nutrient in a form that remains available to the first plant life; harvesting a first harvested portion of an increased biomass of the first plant life that results from the applying; removing a first returnable portion from the first harvested portion to leave a remainder of the first harvested portion, and spreading the first returnable portion on the water surface; and processing the remainder of the first harvested portion into a biofuel component.

U.S. Pat. No. 7,479,167 and U.S. Pat. No. 7,985,267 specifically describe in order to increase seaweed biomass fertilization of the open ocean with a fertilizer system that comprises one or more fertilizers and suitable plant systems is necessary for production of biofuels from seaweed biomass.

WO2011/027360A1 (CSMCRI) describes a process for producing ethanol and seaweed sap from the red seaweed *Kappaphycus alvalrezii*, wherein the process comprises harvesting the *kappaphycus* seaweed, extracting the sap to leave carrageenan rich granules, then washing the granules to remove salt and silt before using acid to hydrolyse the carbohydrates to fermentable sugars followed by neutralization of the acid, removal of the salts by electrodialyis followed by fermentation using yeast. The process described in this patent application emphasizes the removal of salts principally because the salts are inhibitory to the fermentation by the yeast to ethanol.

WO2008/105618A1 (Korea institute of industrial technology) describes production of ethanol from red Seaweed *Gelidium amansii*. The seaweed was prepared first by washing dried seaweed with distilled water, followed by drying and pulverizing, before hydrolysis using acid or enzymatic means in aqueous solutions that do not contain any added salt.

WO2010/098585 describes a method for production of biofuels from seaweed extracts by hydrolysing the extract in a presence of a heterogeneous catalyst and converting the hydrolysate through enzymatic fermentation or chemical reaction into the biofuels. The process described in the application uses extract of the seaweed for producing biofuels. The seaweeds biomass as such has not been used in the process.

Goh and Lee (C. S. Goh, K. T. Lee; A visionary and conceptual macroalgae-based third generation bioethanol (TGB) biorefinery in Sabah, Malaysia as an underlay for renewable and sustainable development, Renewable and Sustainable Energy Reviews 14; 2010; 842-848) describes the hypothetical potential to produce ethanol and other by products from the seaweed *Euchema* spp. The authors describe a flow diagram for the process which suggested that the seaweed be first dried, and then powdered before being processed to various by-products, including ethanol. Goh and Lee further describe in detail as to how the seaweed may first be dried and subsequently the dried seaweed may be transported by boat and that the seaweed should be desalinated otherwise problems could be caused during purification.

Thus, the most of the processes for production of seaweed biomass known in the prior art describe removal of salt from the seaweed before further processing. Further, freshwater and/or fertilizer have been used in the cultivation of seaweeds and further processing of seaweed for producing useful chemicals and biofuel.

Furthermore, it is clear from the above that while the cultivation of seaweeds in the sea avoids the requirements for fertilizer and fresh water during cultivation, the above observations represent the commonly held views on how seaweeds may be collected and processed. Current scientific information suggests that the downstream process, starting with drying and transportation followed by hydrolysis and fermentation are carried out in a conventional manner, using freshwater that is not different from the way land based agricultural biomass is treated. Such processes at a large scale, using large amounts of fresh water and generating correspondingly large amounts of waste to be disposed off are not scalable and sustainable. Therefore, there is a need to provide a cost effective, an easy, sustainable, less time consuming process for production of biofules from seaweed biomass.

Any publications discussed above and throughout the text are provided solely for their disclosure prior to the filing date of the present application. Nothing herein is to be construed as an admission that the inventors are not entitled to antedate such disclosure by virtue of prior disclosure.

SUMMARY OF THE INVENTION

An aspect of the present invention relates to a process for production of one or more renewable chemicals or biofuel from seaweeds, wherein said process comprises providing seaweed slurry prepared in its own fluids or in seawater, wherein the slurry exhibits an ionic conductivity of at least 10,000 micro Siemens, subjecting the slurry having the ionic conductivity to chemical, microbial or thermal treatment to obtain one or more renewable chemicals or biofuel; and recovering the renewable chemicals or biofuel.

OBJECTIVES OF THE INVENTION

One of the objects of the present invention is to provide a cost effective, sustainable and reproducible process to produce renewable chemicals and/or biofuel from seaweed, wherein the process does not use scarce freshwater and fertilizer resources in the process of production of these chemicals.

Another object of the present invention is to provide an environmentally acceptable and energy efficient process to produce renewable industrial chemicals and biofuel from seaweed, recover the same with improved efficiency and with an easy method of disposing of the waste streams.

Furthermore, since handling high quantities of biomass and conveying it over distances at very large scales of operation is logistically difficult, it is a further object of the present invention to provide an easy means of carrying out such operations.

The overall objective of the present invention is to provide a scalable and sustainable process for production of renewable chemicals and biofuel from seaweed.

BRIEF DESCRIPTION OF THE ACCOMPANYING DRAWINGS

The following drawings form part of the present specification and are included to further illustrate aspects of the present invention. The invention may be better understood by reference to the drawings in combination with the detailed description of the specific embodiments presented herein.

FIG. 6

Figure 1:
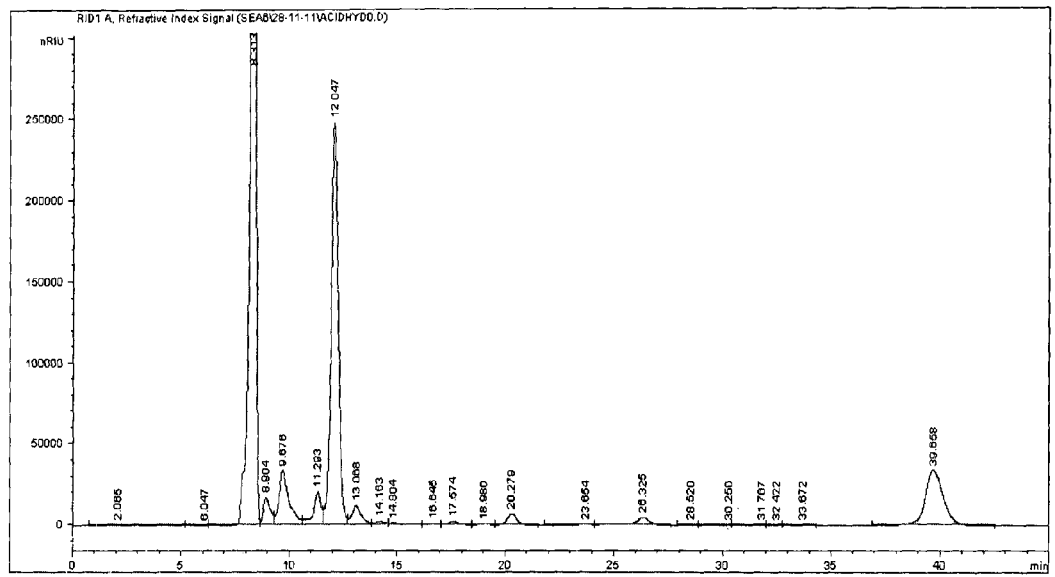
FIG. 1 shows chromatogram showing the various sugars present in 10% (w/v) *Kappaphycus* seaweed acid hydrolysate.

A) Illustrates how salt containing process waste settles down in a column of seawater B) Illustrates how non-salt containing process (freshwater based process) waste forms a buoyant plume and rises to the sea surface in seawater.

DETAILED DESCRIPTION OF THE INVENTION

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of the steps or features.

DEFINITION

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article.

The term "seaweed" used herein encompasses macroscopic, multicellular, benthic marine algae. The term further includes members of the red, brown and green algae and sea-plants.

The use of the term "biomass" herein is by definition limited to seaweeds.

The terms "comprise" and "comprising" are used in the inclusive, open sense, meaning that additional elements may be included. It is not intended to be construed as "consists of only."

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to." "Including" and "including but not limited to" are used interchangeably.

The present invention is not to be limited in scope by the specific embodiments described herein, which are intended for the purposes of exemplification only.

Functionally-equivalent products, compositions, and methods are clearly within the scope of the invention, as described herein.

Several compelling issues drive to develop and improve technology to make biofuels. Dependence on petroleum for fuelling the transportation sector threatens the natural energy sources, affects the environment, and weakens the economy. Developing the technology to produce and use biofuels will help in creating transportation fuel options that can positively impact these issues and establish safe, clean, sustainable alternatives to petroleum. In order to achieve this objective it is necessary to have a cost effective, reproducible, sustainable and scalable process for production of biofuels.

In view of the above the present invention discloses a cost effective, scalable, sustainable, and reproducible process for producing renewable chemicals and/or biofuel from seaweed either in its own salt containing fluids and/or using seawater as the natural processing medium instead of fresh water. The process disclosed in the present invention comprises preparing slurry of the seaweed selected from a group consisting of red algae, brown algae, green algae or a combination thereof without desalination of the seaweed, hydrolyzing the slurry to obtain a hydrolysate comprising fermentable sugar and producing biofuel and/or renewable chemicals from the hydrolysate using the conventional method and recovering the product.

We have found surprisingly, that it is possible to develop a procedure whereby the whole process of producing biofuel such as ethanol and other useful by products from seaweed selected from a group consisting of red algae, brown algae, green algae or a combination thereof can be carried out in a simple and efficient manner without having to remove the salt from the seaweed and using seawater as the natural processing medium instead of fresh water. We have noticed that the seaweed such as *Kappaphycus* when slurried using simple mechanical means either in its own salt containing fluids or in seawater undergoes a significant reduction in volume, which makes its transportation easier. Moreover, the slurry that can be formed can be easily pumped for further processing using pipelines, thus simplifying the handling and transportation of the biomass. We have also found that it is possible to carry out the hydrolysis of the *Kappaphycus* seaweed slurry in sea water to fermentable sugars, without having to separate the solids from the salt containing sap and that it is also possible to ferment the hydrolysate to ethanol in a sea water containing system using specially isolated strains of salt water tolerant organisms. When the ethanol is produced in seawater, it can also be recovered with greater energy efficiency than if the fermentation were carried out using fresh water as a processing medium. Furthermore, we have also discovered that the disposal of the waste products into the sea, after processing, can be carried out much more simply in this case when using seawater as a processing medium, than if the waste products were produced using a fresh water based processing medium. All of the above observations when combined results in the novel and scalable and sustainable method of processing red seaweed species into fuel and fermentable sugars or other by products, in a completely sea-water medium without any additional use of fresh water. It is possible that such observations may also apply to other species of seaweed like brown or green seaweeds.

The seaweeds used in the process of production of renewable chemicals and/or biofuels as disclosed in the present invention were grown using an off shore cultivation system using only seawater followed by harvesting the salt containing wet seaweed biomass offshore and converting it by simple mechanical means into a slurry containing at least 2% solids without desalination and of a pump-able consistency using only the salt containing fluids present in the seaweed or by addition of seawater and conveying the pump-able slurry for further processing. No additional nutrients and/or fertilizers have been used for cultivation of seaweeds.

The pumpable slurry thus obtained was optionally adjusted for the solids content of the slurry to an acceptable level for further processing by using any appropriate dewatering technique like decantation, but only to an extent that it still retains its pumpable characteristics and does not form any powder residue. The slurry was further subjected to hydrothermal treatments to directly produce hydrocarbons like methane or other bio-oils or green crude. Alternatively, the slurry was treated with an appropriate mixture of salt tolerant enzymes or hydrolysing agents to hydrolyse the carbohydrate components to release fermentable sugars into the salt containing aqueous medium and optionally isolating any by products. The released sugars was further converted in the salt containing fluid medium to value added products like ethanol, or other organic chemicals using appropriate salt tolerant microorganisms. The value added products like ethanol could be recovered with greater efficiency than if they were produced using a non-salt containing medium. The waste fluid products obtained in the process after recovery of the value added product were optionally processed further to recover additional by-products like fertilizer. The processed wastes were disposed in a secure manner offshore for example by using off-shore marine outfall deep water disposal techniques such that the waste products did not float up to the surface of the sea as a buoyant plume of waste when released under the sea surface.

In accordance with the present invention in one of the embodiment there is provided a process for producing biofuel from seaweed selected from a group consisting of red algae, brown algae, green algae or a combination thereof, wherein the process comprising preparing a slurry of the seaweed without removing salts from the seaweed, wherein the slurry contains at least 2-60% solids; hydrolyzing the slurry to obtain a hydrolysate comprising fermentable sugar; and producing biofuel from the hydrolysate through enzymatic fermentation or chemical reaction.

In certain embodiment of the present invention there is provided a process for producing biofuel from seaweed selected from a group consisting of red algae, brown algae, green algae or a combination thereof, wherein the process comprising preparing a slurry of the seaweed without removing salts from the seaweed, wherein the slurry contains at least 2-60% solids; and subjecting the slurry to hydrothermal treatment to produce biofuel.

In certain embodiment of the present invention there is provided a process for producing fermentable sugars from seaweed selected from a group consisting of red algae, brown algae, green algae or a combination thereof, wherein the process comprising preparing a slurry of the seaweed without removing salts from the seaweed, wherein the slurry contains at least 2-60% solids; hydrolyzing the slurry to obtain a hydrolysate comprising fermentable sugar; and purifying the fermentable sugars from the hydrolysate.

In another embodiment of the present invention there is provided a process for preparation of seaweed biomass from seaweed selected from a group consisting of red algae, brown algae, green algae or a combination thereof suitable for production of fermentable sugars, sugar acid, sugar alcohols and/or biofuel, wherein the process comprising preparing a slurry of the seaweed without removing salts from the seaweed, wherein the slurry contains at least 2-60% solids.

Certain embodiment of the present invention relates to a process of producing biofuel from seaweed selected from a group consisting of red algae, brown algae, green algae or a combination thereof, wherein the process comprising preparing a slurry of the seaweed without removing salts from the seaweed and further processing the slurry to obtain to produce biofuel, wherein the biofuel is selected from a group consisting of methane, ethanol, butanol, bio-oils, and green crude.

Another embodiment of the present invention relates to a process of producing biofuel from seaweed selected from a group consisting of red algae, brown algae, green algae or a combination thereof, wherein the process comprising preparing a, slurry of the seaweed without removing salts from the seaweed and further processing the slurry to obtain biofuel, wherein the biofuel comprises oxygen containing compound or a bio-hydrocarbon.

Certain embodiment of the present invention relates to a process of producing biofuel from seaweed selected from a group consisting of red algae, brown algae, green algae or a combination thereof, wherein the process comprising preparing a slurry of the seaweed without removing salts from the seaweed and further processing the slurry to obtain biofuel, wherein the biofuel comprises oxygen containing compound selected from a group consisting of ethanol, propanol, butanol, pentanol, hexanol, and a combination thereof.

In certain embodiment of the present invention there is provided a process of producing biofuel from seaweed selected from a group consisting of red algae, brown algae, green algae or a combination thereof, wherein the process comprising preparing a slurry of the seaweed without removing salts from the seaweed and further processing the slurry to obtain biofuel, wherein the biofuel comprises a bio-hydrocarbon selected from a group consisting of gasoline, diesel and Kerosene.

Certain embodiment of the present invention relates to a process for producing biofuel from seaweed selected from a group consisting of red algae, brown algae, green algae or a combination thereof, wherein the process comprising preparing a slurry of the seaweed without removing salts from the seaweed; and subjecting the slurry to hydrothermal treatment to produce biofuel, wherein the hydrothermal treatment is carried out in presence of a catalyst.

One embodiment of the present invention relates to seaweed biomass slurry that is prepared in presence of native salt of seaweeds and/or sea water.

In a preferred embodiment of the present invention there is provided a process for production of one or more renewable chemicals or biofuel from seaweeds, wherein the process comprises providing seaweed slurry prepared in its own fluids or in seawater, wherein the slurry exhibits an ionic conductivity of at least 10,000 micro Siemens, subjecting the slurry having the ionic conductivity to chemical, microbial or thermal treatment to obtain one or more renewable chemicals or biofuel; and recovering the renewable chemicals or biofuel.

The seaweed slurry used in the process for production of one or more renewable chemicals or biofuel from seaweeds comprises at least 2-60% solids.

Another embodiment of the present invention provides a process for production of one or more renewable chemicals or biofuel from seaweeds, wherein the process comprises providing seaweed slurry prepared in its own fluids or in seawater, wherein the slurry exhibits an ionic conductivity of at least 10,000 micro Siemens, subjecting the slurry having the ionic conductivity to chemical treatment without any further treatment to obtain hydrolysate having at least 10,000 micro Siemens of ionic conductivity to obtain one or more renewable chemicals and recovering the renewable chemicals.

The hydrolysate thus obtained can be further used for production of biofuel. For example the hydrolysate can be subjected to fermentation with salt tolerant microorganism to obtain biofuel.

Another embodiment of the present invention provides hydrolysate obtained from the seaweed slurry, wherein said hydrolysate comprises galactose, anhydrogalactose, glucose, xylose, mannose, fructose, glucronic acid, fucose, or mannitol or a combination thereof.

Another embodiment of the present invention provides a process for production of one or more renewable chemicals or biofuel from seaweeds, wherein the process comprises providing seaweed slurry prepared in its own fluids or in seawater, wherein the slurry exhibits an ionic conductivity of at least 10,000 micro Siemens, subjecting the slurry having the ionic conductivity to hydrolysis at a temperature ranging from 10° C. to 180° C. at a pressure of about 0.5 atm to 10 atm, without any further treatment to obtain hydrolysate having at least 10,000 micro Siemens of ionic conductivity to obtain one or more renewable chemicals and recovering the renewable chemicals.

Another embodiment of the present invention provides a process for production of one or more renewable chemicals or biofuel from seaweeds, wherein the process comprises providing seaweed slurry prepared in its own fluids or in seawater, wherein the slurry exhibits an ionic conductivity of at least 10,000 micro Siemens, subjecting the slurry having the ionic conductivity to hydrolysis at a temperature ranging from 20° C. to 120° C. at a pressure of about 0.5 atm to 10 atm, without any further treatment to obtain hydrolysate having at least 10,000 micro Siemens of ionic conductivity to obtain one or more renewable chemicals and recovering the renewable chemicals.

The process for production of one or more renewable chemicals or biofuel from seaweeds using the seaweed slurry as disclosed in the present invention is subjected to acid or enzymatic hydrolysis reaction to obtain hydrolysate comprising renewable chemicals selected from a group consisting of galactose, anhydrogalactose, glucose, xylose, mannose, fructose, glucronic acid, fucose, mannitol and a combination thereof.

The process for production of one or more renewable chemicals or biofuel from seaweeds using the seaweed slurry as disclosed in the present invention can be directly subjected to microbial treatment to obtain biofuel, wherein the microbial treatment is carried out by salt tolerant microorganism such as salt tolerant yeast.

One of the embodiments of the present invention relates to salt tolerant microorganism selected from a group consisting of yeast and bacteria.

Examples of salt tolerant yeast includes but not limited to *Saccharomyces* species, *Saccharomyces cerevisiae*, *Candida* species, *Yarrowia* species, *Rhodotorula* species.

Examples of salt tolerant bacteria includes but not limited to *Vibrio* species, *Staphylococcus* species, *Brevibacterium* species, *Pseudomonas* species and *Bacillus* species.

Another embodiment of the present invention provides a process for production of one or more renewable chemicals or biofuel from seaweeds, wherein the process comprises obtaining the renewable chemicals or biofuel from seaweed slurry prepared in its own fluids or in seawater, wherein the slurry comprises at least 2-60% solids having at least 10,000 micro Siemens of ionic conductivity.

Another embodiment of the present invention provides renewable chemical selected from a group consisting of fermentable sugars, sugar acid and sugar alcohols.

Another embodiment of the present invention provides biofuel selected from a group consisting of methane, ethanol, butanol, bio-oils, and green crude.

Yet another embodiment of the present invention provides biofuel comprising oxygen containing compound or a bio-hydrocarbon.

Further embodiment of the present invention provides oxygen containing compound selected from a group consisting of ethanol, propanol, butanol, pentanol, hexanol, and a combination thereof.

Further embodiment of the present invention provides bio-hydrocarbon selected from a group consisting of gasoline, diesel, and kerosene.

Still another embodiment of the present invention provides a process for production of one or more renewable chemicals or biofuel from seaweeds, wherein the process comprises obtaining the renewable chemicals from seaweed slurry prepared in its own fluids or in seawater and purifying said renewable chemicals wherein the slurry comprises at least 2-60% solids having at least 10,000 micro Siemens of ionic conductivity.

The unique feature of the process for production of one or more renewable chemicals or biofuel from seaweeds without desalination of the seaweed is that the waste stream obtained in the process when disposed in sea it does not form a buoyant plume in the sea-water, thus making the process more eco-friendly.

One embodiment of the present invention provides seaweed selected from a group consisting of red algae, brown algae and green algae.

Examples of seaweed includes but is not limited to *Kappaphycus, Gracillaria, Cyanidioschyzonmerolae, Rhodella, Compsopogon, Stylonema, Bangia, Porphyra, Porphyridium, Hildenbrandia, Nemalion, Corallinaofficinalis, Ahnfeltia, Gelidium Atractophorahypnoides, Gelidiellacalcicola, Lemanea, Palmariapalmata, Schmitziahiscockiana, Chondruscrispus, Mastocarpusstellatus Vanvoorstiabennettiana, Saccharinalatissima*, kelp, *Sargassum, Macrocystis, Ulva*, and *Enteronzorph*.

In another embodiment of the present invention there is provided a biofuel or renewable chemical produced by the process as disclosed whereby the recovery of the biofuel or renewable chemical from the fermentation broth is rendered more efficient because of the salt present in the fermentation broth.

In another embodiment of the present invention there is provided by-product resulted from the process as disclosed in the present invention, wherein the by-product is selected from a group consisting of cattle fodder, aquaculture feed, human nutritional supplements, plant growth promoters, or fertilizers comprising a biofuel component residual that resulted from the process, isolated seaweed protein or hydrolysate thereof, seaweed juices, and microbial fermentation residues from the processing of seaweed.

In order to obtain seaweed biomass for large scale production of renewable chemicals, and/or biofuels, various seaweed cultivation methods can be employed. For example offshore cultivation of seaweed in Bamboo rafts and flexible trusses made of HDPE pipes. Such cultivation method gives good yields of seaweeds and also does not require any additional usage of fresh water or fertilizer. However, other method well known in the art can also be used. Further, the seaweeds can also be collected from naturally occurring seaweed growth.

The seaweeds thus obtained were converted into slurry by mechanical means without desalination. The slurry thus obtained was adjusted to the appropriate solids concentration subjected to hydrolysis to obtain a hydrolysate comprising fermentable sugar. The fermentable sugars thus obtained can be further processed by microbial fermentation or chemical reaction to produce biofuel. Alternatively, the slurry with the appropriate solids concentration was directly subjected to hydrothermal treatments to yield biofuel.

In one of the embodiment of the present invention, there is provided a process for production of one or more renewable chemicals or biofuel from seaweeds, wherein said process comprises providing seaweed slurry comprising at least 2-60% solids, wherein the slurry is prepared in its own fluids or in seawater, with an ionic conductivity between 10,000 and 200,000 micro Siemens. Subjecting the slurry to hydrolysis or hydrothermal treatment to obtain a renewable chemicals or biofuel; and recovering the renewable chemicals or biofuel from the hydrolysate, wherein the renewable chemical is selected from a group consisting of fermentable sugars, sugar acid and sugar alcohols.

In another embodiment of the present invention there is provided a process for, production of one or more renewable chemicals or biofuel from seaweeds, wherein said process comprises providing seaweed slurry comprising at least 2-60% solids, wherein the slurry is prepared in its own fluids or in seawater, with an ionic conductivity between 10,000 and 200,000 micro Siemens, subjecting the slurry to hydrolysis at a temperature ranging from 10° C. to 180° C. at a pressure of about 0.5 atm to 10 atm or hydrothermal treatment at a temperature ranging from 100° C. to 400° C. and a pressure between 1 atm to 300 atm to obtain a renewable chemicals or biofuel; and recovering the renewable chemicals or biofuel from the hydrolysate, wherein the renewable chemical is selected from a group consisting of fermentable sugars, sugar acid and sugar alcohols.

In another embodiment of the present invention there is provided a process for production of one or more renewable chemicals or biofuel from seaweeds, wherein said process comprises providing seaweed slurry comprising at least 2-60% solids, wherein the slurry is prepared in its own fluids or in seawater, subjecting the slurry to hydrolysis at a temperature ranging from 20° C. to 120° C. at a pressure of about 0.5 atm to 10 atm or hydrothermal gasification to obtain a renewable chemicals or biofuel; and recovering the renewable chemicals or biofuel from the hydrolysate, wherein the renewable, chemical is selected from a group consisting of fermentable sugars, sugar acid and sugar alcohols.

The seaweed slurry as disclosed in the present invention is processed further without any further treatment with fresh water to separate, remove, wash or dilute the salts from said slurry.

In one of the embodiment of the present invention, there is provided a process for production of one or more renewable chemicals or biofuel from seaweeds, wherein said process comprises providing seaweed slurry comprising at least 2-60% solids, wherein the slurry is prepared in its own fluids or in seawater, subjecting the slurry to hydrolysis or hydrothermal treatment to obtain a renewable chemicals or biofuel; recovering the renewable chemicals or biofuel from the hydrolysate, and disposing the waste stream obtained in the process, wherein said waste stream does not form a buoyant plume in the sea-water wherein the renewable chemical is selected from a group consisting of fermentable sugars, sugar acid and sugar alcohols.

ADVANTAGES OF THE PRESENT INVENTION

As described above the process of production of renewable chemicals and/or biofuels from seaweeds without removing salts from the seaweeds and/using seawater as a natural is an eco-friendly process with more efficient product recovery and an easy and eco-friendly method of disposing of the waste streams. Further, the process as disclosed in the present invention is cost effective, since transporting and storing the raw material obtained in the form of slurry of the seaweeds because of its lesser bulk is easy, easier handling due to its free flowing nature and its direct use for further processing to obtain renewable chemicals and/or biofuel.

Although the subject matter has been described in considerable detail with reference to certain preferred embodiments thereof, other embodiments are possible. As such, the spirit and scope of the appended claims should not be limited to the description of the preferred embodiment contained therein.

EXAMPLES

The disclosure will now be illustrated with working examples, which is intended to illustrate the working of disclosure and not intended to take restrictively to imply any limitations on the scope of the present disclosure.

Example 1

Offshore Cultivation of *Kappaphycus* and *Ulva* Seaweed

Seaweed *Kappaphycus alvarezii* was cultivated using floating bamboo rafts of the size 3 m×3 m off. The seaweeds were obtained from the coast of Rameswaram, Tamil Nadu, India. The rafts were seeded and left in the sea for a period of 3 months and the seaweed was allowed to grow in the seawater and no additional nutrients were added. After the growth period the seaweed was harvested and sent for processing. About 300 kg of seaweed was obtained from each raft.

In another example, flexible floating truss structure of approximately 9.4 square meters made of HDPE pipes was seeded with *Kappaphycus alvarezii* and anchored off-shore at Mullaikadu Tamil Nadu India. The seaweed was allowed to grow for 30 days and during this period no fertilizers or nutrients were added. After 30 days, the seaweed was harvested. About 250 kg of seaweed was obtained from 9.4 square meters.

In another example, seaweed *Ulva* was collected from an offshore cultivation structure, near Colachel, Tamil Nadu, wherein the *Ulva* had grown naturally on the ropes attached to the offshore cultivation structure. About 2 kg of seaweed *Ulva* was harvested from this structure.

Example 2

Preparation of Seaweed Slurry Having High Salt Concentration and Reduction in Volume for Storage Freshly harvested seaweed *Kappaphycus* was broken into smaller pieces and put into a steel blending jar of a kitchen blender which was equipped with rapidly rotating blades capable of shredding the biomass. The capacity of the blending jar was approximately 1000 ml. About 300 g of seaweed pieces completely filled up the blending jar. The lid of the blending jar was then closed and the blender was switched on for about a minute. There was no addition of any external fluid at any time during the blending process. Upon opening the blending jar, it was observed that the seaweed pieces had been completely converted into compact slurry and the volume of the slurry was approximately 280 ml, which is about one third of the original volume of non-slurried seaweed. Thus, it can be seen that a simple mechanical process can reduce the volume of a given weight of wet seaweed to a great extent thus allowing for compact storage of the harvested seaweed biomass.

Seaweed slurry from *Kappaphycus alvarezii* and *Ulva* can also be prepared from dried seaweed. The dried seaweed can be mixed with seawater to obtain the slurry as described above.

Example 3

Transportation of Seaweed Slurry

About 750 ml of seaweed slurry made as described above was transferred to a glass beaker and put on a laboratory bench, which was about 3 feet high. An empty glass beaker was put on the floor below and a simple siphon arrangement was set up using a silicone pipe of inner diameter 8 mm. About 600 ml of the seaweed slurry was piped from one beaker to another using the set up mentioned above in about 12 seconds. It was found that the slurry flowed easily through the pipe under its own weight, clearly demonstrating the free flowing characteristics of the slurry and its ability to be transported through a pipe from one container to another thus simplifying transportation.

Example 4

Determination of Ionic Strength of Seaweed Slurry

Conductivity is a measure of total ions in solution and is a measure of the total dissolved salts in the solution. The ionic strength of the above mentioned seaweed slurry was measured in terms of conductivity and was compared with deionised water and sea water. The ionic conductivity was measured by using a Eutech PCD650 probe and the conductivity was measured in micro Siemens.

The conductivity of the deionised water was found to be 18 micro Siemens. The conductivity of tap water was found to be 677 micro Siemens. The conductivity of a 1% solution of sea salts in deionized water was found to be 14720 micro Siemens. The conductivity of 3.5% solution of sea salts in deionized water was found to be 52580 micro Siemens. The conductivity of 15% solution of sea salts in deionized water was found to be 169200 micro Siemens.

The conductivity of a sample of seawater from Rameswaram, Tamil Nadu was found to be 62250 micro Siemens. The conductivity of a sample of seawater obtained from Colachel, Kanyakumari District, Tamil Nadu, India was found to be 55790 micro Siemens. The conductivity of a sample of seawater obtained from Tuticorin, TamilNadu, India was found to be 54820 micro Siemes.

The conductivity of the freshly harvested seaweed *Kappaphycus* slurry prepared as described in Example 2 was found to be 80670 micro Siemens. The conductivity of *Kappaphycus* slurry of 16% solids content as prepared from dried seaweed as described in Example 2 was found to be 113800 micro Siemens. It can be seen that the conductivity of seaweed slurry and Seawater are many thousand fold more conductive than deionized water. This clearly demonstrates that the slurry has a high ionic strength and contains lot of dissolved salts.

Example 5

Hydrolysis
1. Acid Hydrolysis of Seaweed Slurry for Production of Fermentable Sugars

*Kappaphycus*:

*Kappaphycus* slurry was prepared as the process as described in Example 2 and was adjusted to the 10% solids by removing part, of the liquid part of the slurry to obtain a suspension. The suspension was subjected to acid hydrolysis reaction by adding 0.1-1N HCl for 20 minutes at 121° to obtain a hydrolysate containing fermentable sugars. Ionic conductivity of the slurry was measured and it was found to be 104,200 micro Siemens. The sugars thus obtained were analysed using HPLC equipped with a refractive index detector. The analysis was performed using Aminex HPX-87H column at 55° C. with 0.01 N H2SO4 as mobile phase. The major sugars detected were galactose (18.8 g/L; retention time: 12.047 min) along with 5-Hydroxymethyl furfural as estimated by HPLC: 8.8 g/L (retention time: 39.658 min) and glucose (1.95 g/L; retention time: 11.293 min) (FIG. 1).

Figure 2:
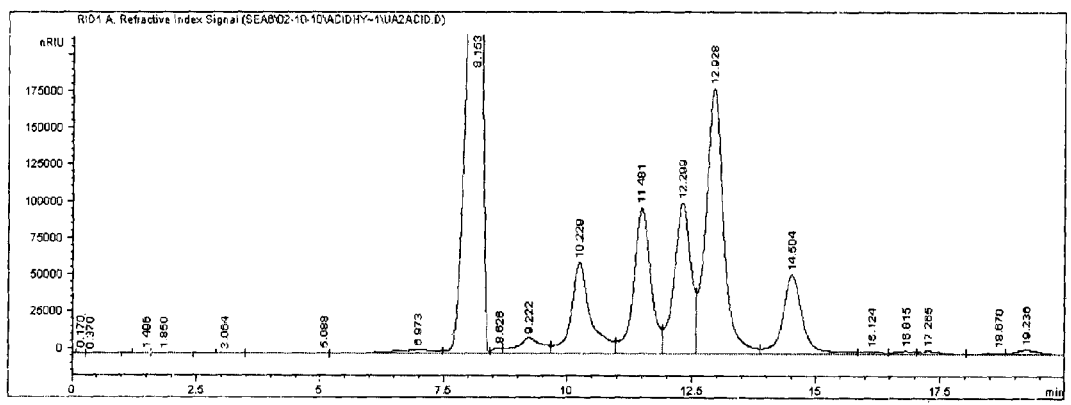
FIG. 2 shows chromatogram showing the various sugars present in the 20% (w/v) *Ulva* acid hydrolysate.

*Ulva*:

A 20% biomass slurry of *Ulva* prepared using the process as described in Example 2. The slurry was treated with 0.4 N $H_2SO_4$ at 121° C. for 20 minutes to obtain a hydrolysate containing fermentable sugars. Ionic conductivity of the slurry was measured and it was found to be 60,880 micro Siemens. The sugars thus obtained were analysed using HPLC equipped with a refractive index detector. The analysis was performed using Aminex HPX-87H column at 55° C. with 0.01 N H2SO4 as mobile phase. The major sugars detected were glucose 10.71 g/L (retention time 11.481 minutes), Galactose/Xylose 8.21 g/L (retention time 12.299 minutes), the peak at 14.504 being the tracer xylitol, and unknown peaks at 10.229 minutes and 12.928 minutes (FIG. 2).

2. Enzyme Hydrolysis of Seaweed Slurry for Production of Fermentable Sugars

A solution of carrageenase enzyme was prepared with a concentration of 0.98 mg/ml. Ten ml of 1% Carrageenan solution prepared in Seawater (3.5% Salt) and 10 ml of 1% Carrageenan solution prepared in distilled water was treated with two ml of carrageenase. The reaction mixture was incubated at 45° C. After 1 hour, the amount of reducing sugar formed in both the samples was estimated using a DNS method against a standard curve of galactose. It was found that the amount of reducing sugar formed in each case was about 1.18 mg/ml indicating that the presence of 3.5% of salt was not inhibitory to the activity of the carrageenase enzyme.

As described in Example 2, 2% *Kappaphycus alvarezii* slurry was prepared in seawater. Ionic conductivity of the slurry was measured and it was found to be 56,410 micro Siemens. Ten ml of the slurry was treated with 2 ml (0.98 mg/ml) of the salt tolerant carrageenase enzyme and incubated at 45° C. The reaction mixture was mixed every 10-15 min. The reducing sugar concentration after 1 hour and 3 hours of incubation was measured and it was found to be 0.3 mg/ml and 0.4 mg/ml respectively, indicating that the carrageenase enzyme was able to hydrolyze the seaweed slurry having high ionic conductivity.

3. Ionic Liquid Hydrolysis of Seaweed Slurry to Produce Reducing Sugars.

Kappaphycus Seaweed slurry prepared by the process as described in Example 2 and adjusted to 10% biomass concentration exhibiting ionic conductivity of the slurry of 104,200 micro Siemens. The slurry was subjected to ionic liquid hydrolysis by adding 30 mM ionic liquid, Tetrabutyl ammonium hydrogen sulphate followed by incubation at 121° C. for 20 minutes. The reducing sugar content of the hydrolysate was estimated by the DNS and the efficiency of hydrolysis was estimated to be 25%.

Example 6

Biofuel Production from Seaweed Slurry or Hydrolysate
1. Biogas Production: Hydrothermal Gasification *Kappaphycus* Slurry Kappaphycus seaweed slurry was prepared with a solids content of 16.15% (w/v) was prepared using the process as described in Example 2. Conductivity of the slurry was measured and it was found to be 116250 micro Siemens. The slurry was pumped into Catalytic Hydrothermal Gasification equipment at a liquid hourly space velocity of 1.5. The gasification was carried out at an operating temperature of 350° C. and pressure of 3000 psig with ruthenium on carbon extrudate as the catalyst. The gaseous product as monitored by Gas Chromatography at STP showed an overall gas flow rate of 29.5 L/hr comprising of 53.5% by volume of Carbon dioxide and 45.5% by volume of methane. The waste stream from the process with a liquid hourly space velocity of 1.45 L/hr was found to be clear and comprised of 18650 ppm potassium, 6000 ppm sodium, 36750 ppm chloride and 2600 ppm of bromine.

It was thus clearly shown that a salt containing seaweed slurry could be directly converted into a gaseous biofuel along with the recovery of salts in the aqueous waste product stream.

Similarly, hydrothermal liquefaction process can be used for production of liquid fuels from the said seaweed slurry prepared by the process as described in Example 2.

2. Bio-Ethanol Production: Microbial Fermentation of *Kappaphycus* Slurry

Isolation of Salt Tolerant Microorganisms

Salt tolerant microorganisms such as a salt tolerant yeast strain can be used for microbial fermentation of the salt containing seaweed hydrolysates to produce ethanol. In the present invention yeast *Saccharomyces cerevisiae* strain having accession number MTCC 170 was tested using following process for salt tolerance and was used in subsequent experiments.

The carbohydrate fermentation ability of yeast *Saccharomyces cerevisiae* strain having accession number MTCC 170 was tested using Marine oxidation fermentation medium (MOF). The MOF medium was prepared by dissolving 20 g of commercially available (Himedia) MOF medium in 1000 ml distilled water with 1.5% (w/v) agar. The medium was sterilized by autoclaving at 15 lbs, 15 min. Filter sterilized carbohydrate solutions (Glucose and Galactose) were added to the medium when cooled to 55° C. Aliquots of 6 ml of the medium were distributed into culture tubes and autoclaved at 10 lbs for 10 min. and converted to slants. They were inoculated with the culture of the yeast strain by stabbing and streaking. The inoculated tubes were incubated at 28° C. for 48 hours and observed for growth and pH change. The strain was found to be capable of fermenting both glucose and Galactose.

The yeast strain was further screened for its ability to survive and grow in the presence of 5% ethanol in the presence of seawater and its ability to tolerate 150 g/L glucose or 150 g/L galactose in the presence of seawater in the following manner.

The screening experiments were carried out in YEPD medium comprising 10 g/L yeast extract, 20 g/L peptone and either containing 50 g/L of ethanol or 150 g/L Glucose or Galactose with seawater as base.

The initial seed culture was grown aerobically in broth, comprising of 10 g/L yeast extract, 20 g/L peptone and 10 g/L glucose or galactose with seawater as base. 10 ml of the seed culture was inoculated in 100 ml of the YEPD medium such that the final OD of the culture is 1, followed by the incubation of fermentation traps at 30° C. without agitation.

It was found that the yeast strain MTCC 170 remained viable in the presence 50 g/L of ethanol in the presence of seawater, as evidenced by the evolution of carbon dioxide bubbles. It was also found that the strain MTCC 170 was capable of remaining viable in the presence of 150 g/L of Glucose or galactose.

By the sequential isolation and testing process described above in the presence of high concentration of salts like those found in seawater, it is possible to screen microorganisms such as yeast strains capable of producing more ethanol in the presence of seawater and high concentrations sugars, like glucose and galactose. These sugars are typical of the sugars that would be obtained from the hydrolysis of seaweed biomass. Strains capable of producing ethanol and tolerating even higher concentration of salts than that present in normal seawater may also be isolated using the above procedure by adding additional sea salts into the screening medium.

Microbial Fermentation

Hydrolysate obtained from hydrolysis of *Kappphycus* and *ulva* seaweed slurry as described in Example 5 was used as a source of sugars for fermentation using the salt tolerant microorganisms isolated as described above.

Figure 3:
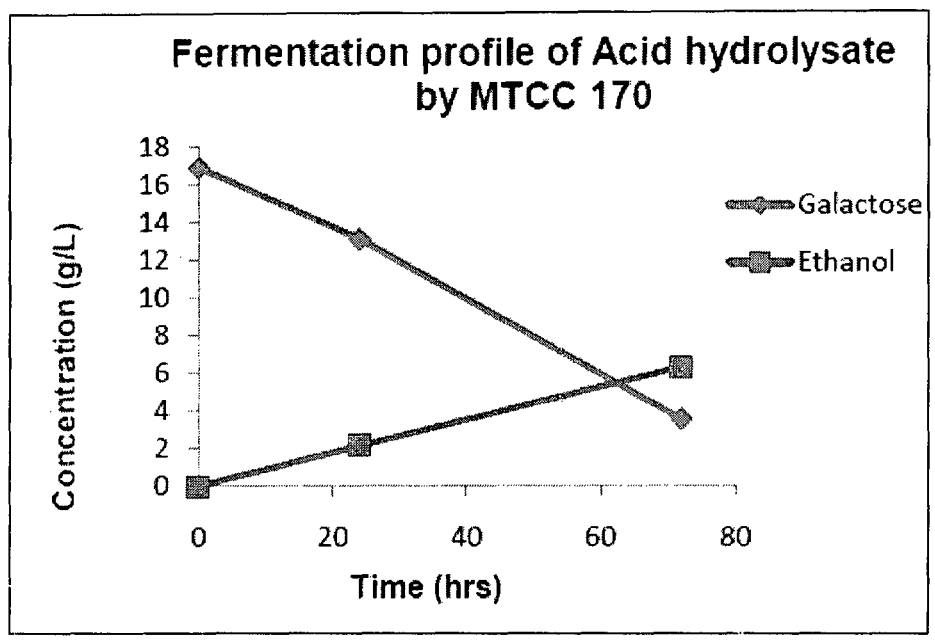
FIG. 3 illustrates production of ethanol from the seaweed acid hydrolysates by the yeast strain MTCC 170.

The selected culture of yeast *Saccharomyces cerevisiae* strain having accession number MTCC 170 capable of fermenting sugars to ethanol in seawater/salt water was inoculated in the hydrolysate obtained using the hydrolysis as described in Example 5. The seaweed hydrolysate was inoculated with the yeast strain and incubated at 30° C. in anaerobic conditions without agitation. Samples were collected periodically and analysed for the production of ethanol (FIG. 3).

Result:

An initial concentration of galactose in the fermentation medium was estimated to be 16.92 mg/ml. After 3 days of fermentation, the residual galactose was 3.54 mg/ml indicating a consumption of 13.38 mg/ml of galactose. The theoretical maximum yield of ethanol for the consumption of this quantity of galactose should be 6.69 mg/ml of ethanol. The actual ethanol concentration was measured as 6.3 mg/ml. Thus, the efficiency of the conversion of galactose to ethanol in the salt containing seaweed hydrolyzate was estimated to be 94%.

Example 7

Improved Efficiency of Product Recovery (Ethanol) in Presence of Seawater

A medium containing 100 g/L galactose, yeast extract 10 g/L and peptone 20 g/L was prepared in seawater (3.5% salts) and autoclaved. The medium was inoculated with a galactose metabolizing salt tolerant yeast strain MTCC 170 isolated using the process described above.

Figure 4:
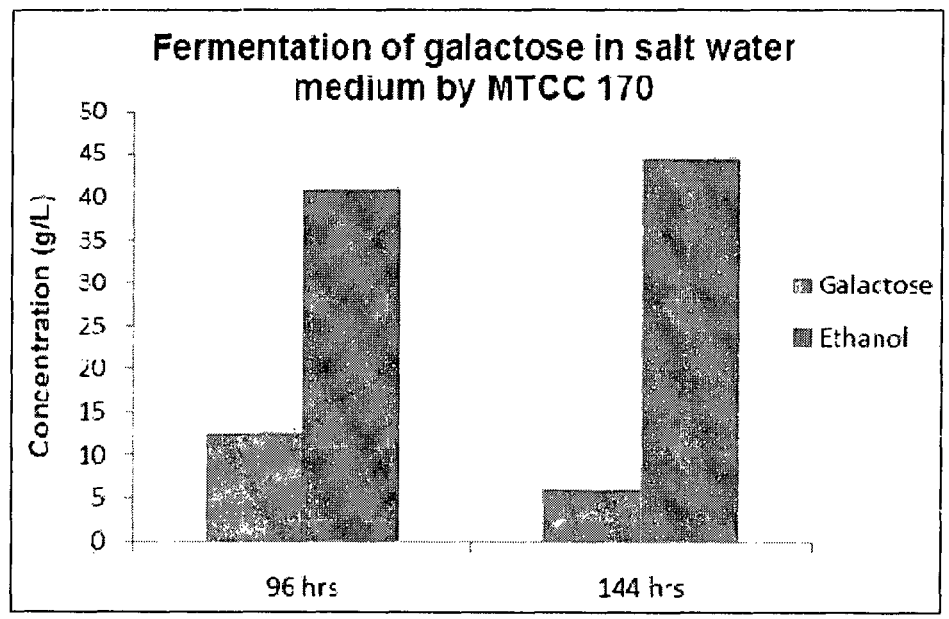
FIG. 4 illustrates production of Ethanol in seawater from Galactose obtained from seaweed.

The ethanol concentration and residual galactose concentration achieved after 96 hours and 144 hours is shown in FIG. 4. About 45 g/L of ethanol was obtained in 144 hours with a residual galactose of 5 g/L, which demonstrated a high ethanol fermentation efficiency of 94%. The ethanol produced after fermentation was recovered by distillation, leaving behind a salt containing spent process waste.

Figure 5:
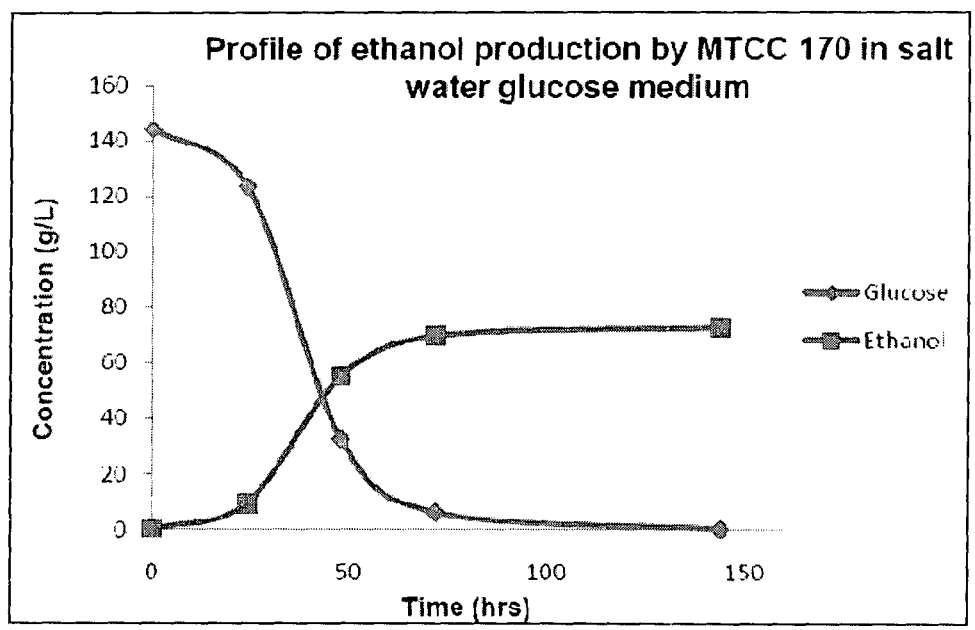
FIG. 5 illustrates Consumption profile of Glucose sugars during ethanol production in seawater medium by a strain of salt and ethanol tolerant yeast

In another experiment, a medium containing 150 g/L glucose, 10 g/L peptone and 20 g/L of yeast extract was made in seawater (3.5% w/v salts) and autoclaved. It was inoculated with a the selected culture of salt tolerant glucose fermenting yeast strain having accession number MTCC 170 produced an ethanol concentration of 70 g/L in 48 hours in the seawater medium and almost completely consumed all the glucose. This represents a fermentation efficiency of 95% (FIG. 5).

Thus, from the above it was concluded that it is possible to carry out very efficient conversion of sugars derived from Seaweed to ethanol in a seawater medium using a salt tolerant yeast strain. The ethanol produced after fermentation was recovered by distillation, leaving behind a salt containing spent process waste.

It can be seen that once each of the constituents of seaweed is broken down to simpler sugars in salt water, using any appropriate method, it is possible to ferment the sugars in a salt water environment to a biofuel like ethanol or another renewable chemical using the appropriate salt tolerant strain of microorganism.

Next, a simulated fermented broth containing ethanol in Seawater prepared to resemble the broth obtained at the end of fermentation as described above. This simulated broth contained 7% (70 g/L) ethanol in seawater medium. In parallel another simulated broth was prepared which contained 7% (70 g/L) ethanol but in a deionized water medium. This broth resembles the kind of fermented broth that would be obtained when deionized water is used as a processing medium instead of seawater. About 100 ml of each of these simulated broths was subjected to distillation to recover the ethanol and the first 10 ml of initial distillate was collected from each of these simulated broths and the concentration of the ethanol in the distillates was measured.

Result:

It was found that the initial distillates from the broth containing the seawater were more concentrated (76.71% v/v) that the initial distillates from the broth made in deionized water (71.763% v/v). The ability to get more concentrated distillates is a process advantage that leads to substantial energy savings. Thus, it could be established that the conversion to biofuel and the recovery of the biofuel or renewable chemical from fermentation from seawater containing broths was more efficient.

Example 8

Easy Disposal of Process Waste after Recovery of Product

The process waste is the material left behind after the conversion of the seaweed biomass to biofuel and the recovery of the biofuel. A tracking dye, saffrarin, was added to the process waste produced after the microbial fermentation and distillation of a solution of sugars containing a high concentration of salt, similar to that present in the hydrolyzate of seaweed biomass slurry. The slurry was prepared by the process as described in Example 2. The dye gives a red colour to the waste. A similar experiment was performed with a non-salt containing process waste. The non-salt containing process waste was prepared by distilling a fermented broth where the sugars were in a fermentation medium that was made in fresh water instead of sea water. Both these process wastes i.e salt containing and the non-salt containing were pumped at a slow flow rate into a tall column of sea-water contained in a cylindrical container to simulate the process of off-shore disposal of the process wastes.

Figure 6:

It could be easily seen that the salt containing process waste would settle down to the bottom of the cylindrical container (FIG. 6A), whereas the non-salt containing process waste tended to float up to the surface in the form of a buoyant plume (FIG. 6B).

The easy settlement of salt containing process wastes (which is a consequence of the whole process being carried out in sea water) allows such waste streams to be safely disposed off and efficiently locked up under the sea surface, and allowed to degrade slowly, quite similar to the way marine life degrades, when it dies and sinks to the bottom of the sea.

In contrast, it is seen that the non-salt containing waste streams (using a fresh water based process) when disposed of similarly, floats up to the top of the sea surface in the form of a buoyant plume. This plume, containing all the waste materials would cause nutrient excess at the surface of the sea resulting in harmful algal blooms and eutrophication which are extremely damaging to the environment.

Normal biofuel and renewable chemical production processes, which are carried out in fresh water, not only consume a lot of fresh water, but also generate a lot of waste streams, which have to be discharged safely, and the expenses involved in treating waste streams are considerable. Carrying out a biofuel or renewable chemical production process in seawater or salt water not only avoids the use of scare fresh water, but also results in a simple waste disposal process. Having a waste disposal process that is simple is not just environmentally friendly, but also economically beneficial to the entire process.

What is claimed is:

1. A process for production of one or more renewable chemicals or biofuel from seaweed, wherein the process comprises:
    (a) harvesting seaweed and mechanically processing the harvested seaweed in the seaweed's own fluids or in seawater, to provide a slurry containing at least 2-60% solids, wherein the slurry exhibits an ionic conductivity of at least 10,000 micro Siemens;
    (b) subjecting the slurry exhibiting said ionic conductivity to hydrolysis by chemical treatment to obtain a hydrolysate exhibiting an ionic conductivity of at least 10,000 micro Siemens, followed by microbial treatment with a salt tolerant microorganism to obtain one or more renewable chemicals or biofuel; and
    (c) recovering the one or more renewable chemicals or biofuel.
2. The process as claimed in claim 1, wherein the hydrolysate comprises galactose, anhydrogalactose, glucose, xylose, mannose, fructose, glucronic acid, fucose, mannitol, or a combination thereof.

3. The process as claimed in claim 1, wherein the slurry is subjected to hydrolysis at a temperature ranging from 10° C. to 180° C. and at a pressure of from about 0.5 atm to 10 atm.

4. The process as claimed in claim 3, wherein the temperature is in the range of from 20° C. to 120° C.

5. The process as claimed in claim 1, where said chemical treatment of the hydrosylate is carried out by reaction with an acid, by reaction with an ionic liquid or by enzymatic hydrolysis with an isolated salt tolerant enzyme.

6. The process as claimed in claim 1, wherein the salt tolerant microorganism is a salt tolerant yeast.

7. A process for production of one or more renewable chemicals or biofuel from seaweed, wherein the process consists essentially of:
(a) harvesting seaweed and mechanically processing the harvested seaweed in the seaweed's own fluids or in seawater to provide a slurry;
wherein the slurry comprises at least 2 to 60% solids and exhibits a conductivity of at least 10,000 micro Siemens,
(b) subjecting the slurry exhibiting said ionic conductivity to microbial treatment with a salt tolerant microorganism,
thereby producing one or more renewable chemicals or biofuel from the harvested seaweed.

8. The process as claimed in claim 7, wherein said renewable chemical is selected from the group consisting of fermentable sugars, sugar acid and sugar alcohols.

9. The process as claimed in claim 7, wherein said biofuel is selected from the group consisting of methane, ethanol, butanol, bio-oils, and green crude.

10. The process as claimed in claim 7, wherein said biofuel comprises an oxygen containing compound or a bio-hydrocarbon.

11. The process as claimed in claim 10, wherein said oxygen containing compound is selected from the group consisting of ethanol, propanol, butanol, pentanol, hexanol, and a combination thereof.

12. The process as claimed in claim 10, wherein said bio-hydrocarbon is selected from the group consisting of gasoline, diesel, and kerosene.

13. The process as claimed in claim 7 wherein said process further comprises purifying said the one or more renewable chemicals.

14. The process as claimed in claim 7, wherein said process further comprises disposing waste stream obtained in the process, wherein said waste stream does not form a buoyant plume in the sea-water.

15. The process as claimed in claim 1 wherein said seaweed is selected from the group consisting of *Kappaphycus, Gracillaria, Cyanidioschyzonmerolae, Rhodella, Compsopogon, Stylonema, Bangia, Porphyra, Porphyridium, Hildenbrandia, Nemalion, Corallinaofficinalis, Ahnfeltia, Gelidium Atractophorahypnoides, Gelidiellacalcicola, Lemanea, Palmariapalmata, Schmitziahiscockiana, Chondruscrispus, Mastocarpusstellatus* and *Vanvoorstiabennettiana*.

16. The process as claimed in claim 1 wherein said seaweed is selected from the group consisting of *Saccharinalatissima*, kelp, *Sargassum* and *Macrocystis*.

17. The process as claimed in claim 1, wherein said seaweed is *Ulva* or *Enteromorpha*.

18. The process as claimed claim 1, wherein said seaweed is *Kappaphycus* or *Ulva*.

19. The process as claimed claim 7, wherein said seaweed is *Kappaphycus* or *Ulva*.

20. A process for production of one or more renewable chemicals or biofuel from seaweed, wherein the process comprises:
(a) harvesting seaweed and mechanically processing the harvested seaweed in the seaweed's own fluids or in seawater to obtain a slurry comprising at least 2-60% solids, where the slurry exhibits an ionic conductivity of at least 10,000 micro Siemens,
(b) subjecting the slurry exhibiting said ionic conductivity to hydrolysis by chemical and thermal treatment to obtain a hydrolysate, followed by microbial treatment with a salt tolerant microorganism to obtain one or more renewable chemicals or biofuel; and
(c) recovering the one or more renewable chemicals or biofuel.

21. The process as claimed in claim 20, wherein said hydrolysate comprises galactose, anhydrogalactose, glucose, xylose, mannose, fructose, glucronic acid, fucose, mannitol or a combination thereof.

22. The process as claimed in claim 20, wherein the slurry is subjected to hydrolysis at a temperature ranging from 100° C. to 180° C. and at a pressure of from about 0.5 atm to about 10 atm.

23. The process as claimed in claim 22, wherein the temperature is in the range of from 20° C. to 120° C.

24. The process as claimed in claim 20, where said chemical treatment of the hydrosylate is carried out by reaction with an acid, by reaction with an ionic liquid or by enzymatic hydrolysis with an isolated salt-tolerant enzyme.

25. The process as claimed in claim 20, wherein the salt tolerant microorganism is a salt tolerant yeast.

* * * * *